US007122338B2

(12) United States Patent
Crouteau et al.

(10) Patent No.: US 7,122,338 B2
(45) Date of Patent: *Oct. 17, 2006

(54) METHOD FOR QUANTIFICATION OF BIOLOGICAL MATERIAL IN A SAMPLE

(75) Inventors: Andrew J. Crouteau, Peabody, MA (US); Mark W. Pierson, Saco, ME (US); David E. Townsend, Scarborough, ME (US); Ali Naqui, Falmouth, ME (US)

(73) Assignee: Biocontrol Systems, Inc., Bellevue, WA (US)

( * ) Notice: Subject to any disclaimer, the term of this patent is extended or adjusted under 35 U.S.C. 154(b) by 462 days.

This patent is subject to a terminal disclaimer.

(21) Appl. No.: 10/349,196

(22) Filed: Jan. 21, 2003

(65) Prior Publication Data
US 2004/0018585 A1 Jan. 29, 2004

Related U.S. Application Data

(63) Continuation-in-part of application No. 09/838,590, filed on Apr. 18, 2001, now Pat. No. 6,509,168, which is a continuation of application No. 09/277,522, filed on Mar. 26, 1999, now Pat. No. 6,287,797, which is a continuation of application No. 08/746,054, filed on Nov. 6, 1996, now Pat. No. 5,985,594, which is a continuation-in-part of application No. 08/606,229, filed on Feb. 23, 1996, now Pat. No. 5,700,655, which is a continuation-in-part of application No. 08/557,529, filed on Nov. 14, 1995, now abandoned.

(51) Int. Cl.
*C12Q 1/24* (2006.01)
(52) U.S. Cl. .................... 435/30; 435/287.9
(58) Field of Classification Search .................. 435/30, 435/287.9
See application file for complete search history.

(56) References Cited

U.S. PATENT DOCUMENTS

| 2,771,398 A | 11/1956 | Snyder ...................... 195/103.5 |
| 3,206,317 A | 9/1965 | Golber ........................ 99/192 |
| 3,356,462 A | 12/1967 | Cooke et al. ................. 23/292 |
| 3,496,066 A | 2/1970 | Berger et al. ............ 195/103.5 |
| 3,649,464 A | 3/1972 | Freeman .................. 435/305.2 |
| 3,787,290 A | 1/1974 | Kaye ...................... 195/103.5 R |
| 3,870,601 A | 3/1975 | Warren et al. ......... 195/103.5 R |
| 4,129,483 A | 12/1978 | Bochner ...................... 195/100 |
| 4,208,480 A | 6/1980 | D'Amato et al. ............. 435/34 |
| 4,235,964 A | 11/1980 | Bochner ...................... 435/34 |
| 4,240,751 A | 12/1980 | Linnecke et al. ........... 356/409 |
| 4,245,043 A | 1/1981 | Lund ........................... 435/33 |
| 4,292,273 A | 9/1981 | Butz et al. .................. 422/102 |
| 4,315,593 A | 2/1982 | Matte .......................... 233/21 |
| 4,495,289 A | 1/1985 | Lyman et al. ............... 435/284 |
| 4,545,958 A | 10/1985 | Dopatka .................... 422/102 |
| 4,560,535 A | 12/1985 | Bouchee .................... 422/102 |
| 4,591,554 A | 5/1986 | Koumura et al. ............. 435/18 |
| 4,622,297 A | 11/1986 | Kappner et al. .............. 435/32 |
| 4,675,289 A | 6/1987 | Kanou et al. ................. 435/18 |
| 4,735,778 A | 4/1988 | Maruyama et al. ......... 422/102 |
| 4,741,619 A | 5/1988 | Humphries et al. ......... 356/246 |
| 4,761,378 A | 8/1988 | Godsey ...................... 435/293 |
| 4,803,162 A | 2/1989 | Smith et al. .................. 435/36 |
| 4,812,409 A | 3/1989 | Babb et al. .................... 435/7 |
| 4,925,789 A | 5/1990 | Edberg ........................ 435/38 |
| 5,004,684 A | 4/1991 | Simpson et al. ............... 435/8 |
| 5,292,644 A | 3/1994 | Berg .......................... 435/29 |
| 5,393,662 A | 2/1995 | Roth et al. ................... 435/38 |
| 5,429,933 A | 7/1995 | Edberg ........................ 435/34 |
| 5,508,005 A | 4/1996 | Mathus ...................... 422/102 |
| 5,518,892 A * | 5/1996 | Naqui et al. ................. 435/29 |
| 5,540,891 A | 7/1996 | Portmann et al. ........... 422/102 |
| 5,635,367 A * | 6/1997 | Lund ........................... 435/34 |
| 5,700,655 A * | 12/1997 | Croteau et al. ............... 435/30 |

(Continued)

FOREIGN PATENT DOCUMENTS

DE  34 19327 A1  5/1984

(Continued)

OTHER PUBLICATIONS

Bacteriological Ambient Water Quality Criteria for Marine and Fresh Recreational Waters, Ambient Water Quality Criteria for Bacteria, USEPA (1986).

(Continued)

*Primary Examiner*—Ralph Gitomer
(74) *Attorney, Agent, or Firm*—Seed IP Law Group PLLC

(57) ABSTRACT

Methods for the detection and/or quantification of a biological material in a sample. The method includes the steps of liquefying the sample (if necessary) and pouring the liquefied sample into the incubation vessel. The incubation vessel has a generally flat horizontal surface and the surface is divided into at least one incubation site. Each incubation site is adapted to hold an aliquot of liquid and is sized and shaped, and formed of a suitable material, to hold the aliquot within the well by surface tension. Any excess liquid from the liquefied sample is poured from the surface of the incubation vessel. The method then involves incubating that incubation vessel until the presence or absence of the biological material is determined. The presence of air bubbles can be dramatically reduced by the presence of a surface acting agent in the liquid sample deposited on the device surface. Such an agent can be added to the sterile diluent used to prepare the test reagent, can be separately added to the test reagent after it is prepared, or can be added to the test sample directly while it is being prepared for testing.

30 Claims, 5 Drawing Sheets

U.S. PATENT DOCUMENTS

| | | | |
|---|---|---|---|
| 5,985,594 A * | 11/1999 | Croteau et al. | 435/30 |
| 6,190,878 B1 * | 2/2001 | Pierson et al. | 435/34 |
| 6,268,209 B1 * | 7/2001 | Pierson et al. | 435/287.9 |
| 6,287,797 B1 * | 9/2001 | Croteau et al. | 435/30 |
| 6,509,168 B1 * | 1/2003 | Croteau et al. | 435/30 |

FOREIGN PATENT DOCUMENTS

| | | |
|---|---|---|
| EP | 25 467 B1 | 3/1981 |
| EP | 59 645 B1 | 9/1982 |
| EP | 305 900 A2 | 3/1989 |
| EP | 332 752 A1 | 9/1989 |
| EP | 542 422 A1 | 5/1993 |
| GB | 2005410 A | 4/1979 |
| GB | 2015729 A | 9/1979 |
| WO | WO 91/09970 | 7/1991 |
| WO | WO 95/23026 | 8/1995 |
| WO | WO 99/34920 * | 7/1999 |

OTHER PUBLICATIONS

Brenner et al., "New Medium for the Simultaneous Detection of Total Coliforms and *Escherichia coli* in Water," Applied and Environmental Microbiology 59:3534-3544 (1993).

Cabelli et al, "A Marine Recreational Water Quality Criterion Consistent with Indicator Concepts and Risk Analysis," Journal WPCF 55:1306-1314 (1983).

Cabelli, "Swimming-Associated Illness and Recreational Water Quality Criteria," *Water Sci. Tech. 21*: 13-21, 1989.

Dahlen and Linde, "Screening Plate Method for Detection of Bacterial β-Glucuronidase," *Applied Microbiology 26*: 863-866, 1973.

Damare et al., "Simplified Direct Plating Method for Enhanced Recovery of *Escherichia coli* on Food," *J. Food Science 50*: 1736-1738, 1985.

de Man, "The Probability of Most Probable Numbers," European J. Appl. Microbiol. 1:67-78 (1975).

Donnelly and Hartman, "Gentamicin-Based Medium for the Isolation of Group D Streptococci and Application of the Medium to Water Analysis," Applied And Environmental Microbiology 35:576-581 (1978).

Gatti and Neviani, "A New Simple Medium for the Detection of Enterococcus Faecalis and Enterococcus Faecium by Measurement of Conductance Changes," Letters in Applied Microbiology 17:72-74 (1993).

Hansen and Yourassowsky, "Detection of β-Glucuronidase in Lactose-Fermenting Members of the Family Enterobacteriaceae and Its Presence in Bacterial Urine Cultures," J. Biol. Chem. 20:1177-1179 (1984).

Hernandez et al., "MPN Miniaturized Procedure for the Enumeration of Faecal Enterococci in Fresh and Marine Waters: The Must Procedure," Wat. Res. 27:597-606 (1993).

Jay (ed.), *Modern Food Microbiology*, 4th ed., Van Nostrand Reinhold, New York, 1992, Chapter 5, "Culture, Microscopic, and Sampling Methods," pp. 113-121.

Kendall et al., "Observations of the Relative Constancy of Ammonia Production by Certain Bacteria," J. Infectious Diseases 13:425-428 (1913).

Kilian and Bülow, "Rapid Identification of Enterobacteriaceae," Acta Path. Microbiol. Scand. Section B 87:271-276 (1979).

Knudtson and Hartman, "Comparison of Fluorescent Gentamicin-Thallous-Carbonate and KF Streptococcal Agars to Enumerate Enterococci and Fecal Streptococci in Meats," Applied and Environmental Microbiology 59:936-938 (1993).

Littel and Hartman, "Fluorogenic Selective and Differential Medium for Isolation of Fecal Streptococci," Applied and Enviromental Microbiology 45:622-627 (1983).

Maddocks and Greenan, "Technical Method: A Rapid Method for Identifying Bacterial Enzymes," J. Clinical Pathology 28:686-687 (1975).

Mooney et al., Testing the Waters: A National Perspective on Beach Closings, Natural Resources Defense Council, pp. 1-67 (1992).

Peeler et al., *Compendium of Methods for the Microbiological Examination of Foods*, American Public Health Association, Washington, DC, 1992, Chapter 6, "The Most Probable Number Technique," pp. 105-120.

Sarhan and Foster, "A Rapid Fluorogenic Method for the Detection of *Escherichia coli* by the Production of β-glucuronidase," J. Applied Bacteriology 70:394-400 (1991).

Standard Methods for the Examination of Water and Waste Water, 18th ed., American Public Health Association, Washington, DC, 1992, Greenberg et al. eds., pp. 9-69 to 9-73.

Standard Methods for the Examination of Water and Waste Water, 18th ed., American Public Health Association, Washington, DC, 1992, Greenberg et al. eds, pp. 9-45 to 9-64.

Thomas, "Bacterial Densities From Fermentation Tube Tests," J. Am. Water Works Assoc. 34:572-576 (1942).

Trepta and Edberg, "Esculinase (β-glucosidase) for the rapid estimation of activity in bacteria utilizing a hydrolyzable substrate, p-nitrophenyl-β-D-glucopyranoside," Antonie van Leeuwenhoek 53:273-277 (1987).

Trepeta and Edberg, "Methylumbelliferyl-β-D-Glucuronide-Based Medium for Rapid Isolation and Identification of *Escherichia coli*," J. Clinical Microbiology 19:172-174 (1984).

Ur and Brown, "Impedance Monitoring of Bacterial Activity," J. Med. Microbiol. 8:19-28 (1975).

Standard Methods for the Examination of Water and Waste Water, 18th ed., American Public Health Association, Washington, DC, 1992, Greenberg et al. eds., pp. 9-69 to 9-73.

\* cited by examiner

US 7,122,338 B2

METHOD FOR QUANTIFICATION OF BIOLOGICAL MATERIAL IN A SAMPLE

CROSS-REFERENCES TO RELATED APPLICATIONS

This application is a continuation-in-part of U.S. Ser. No. 09/838,590, filed Apr. 18, 2001, now U.S. Pat. No. 6,509,168, which is a continuation of U.S. Ser. No. 09/277,522, filed Mar. 26, 1999, now U.S. Pat. No. 6,287,797, which is a continuation of U.S. Ser. No. 08/746,054, filed Nov. 6, 1996, now U.S. Pat. No. 5,985,594, which is a continuation-in-part of U.S. Ser. No. 08/606,229, filed Feb. 23, 1996, now U.S. Pat. No. 5,700,655, which is a continuation-in-part of U.S. Ser. No. 08/557,529, filed Nov. 14, 1995 now abandoned, all entitled "Method for Quantification of Biological Material in a Sample" hereby incorporated herein by reference, including drawings.

FIELD OF THE INVENTION

This invention relates to a method for quantification of biological material in a sample.

DESCRIPTION OF THE RELATED ART

Many industries need to detect and quantify the concentration and level of biological material in a sample. For example, the determination of bacterial concentration in food and water is an essential part of food and water quality testing. EPA regulations require that no Coliform such as *Escherichia coli* can be present in potable water. The "presence/absence" format of a testing medium, such as Colilert® chemical mixture (IDEXX Laboratories, ME) which is used as a testing medium for *Escherichia coli* and all coliform bacteria, is very useful in making this determination. Colilert® chemical mixture is based on the Defined Substrate Technology described in Edberg, "Method and Medium for use in Detecting Target Microbes In situ in A Specimen Sample of A Possibly Contaminated Material," U.S. Pat. Nos. 4,925,789 and 5,492,933. See also, Townsend et al., U.S. Ser. No. 08/484,593 filed Jun. 7,1995 entitled, "Method and Composition for Detecting Bacterial Contamination in Food Products", hereby incorporated by reference herein, describes a medium for the detection of bacteria in food and water samples.

However, there are areas where the quantification, not just the detection, of bacterial concentration is important. Examples of such areas include waste water, incoming water in water purification systems, surface water, and food testing. For example, numerous restaurant chains will only accept raw ground beef or poultry that contains less than a certain concentration of bacterial contamination. Therefore, food processing plants must carry out the necessary microbiological tests to determine the bacterial concentration of these food items before they can be released to customers.

The classical methods of quantification of biological material are the standard plate count method or the multiple tube fermentation (MTF) method. A quantity of sample being tested for microbial contamination is first dispensed in a Petri-dish. Then 15 ml of the appropriate media is poured over the sample. The Petri-dish is then swirled to mix the sample in the medium and the Petri-dish is left to solidify at room temperature for approximately 20 minutes. The medium is then incubated at a specific temperature for a specific time, and any resulting colonies are counted.

The multiple tube fermentation method is described in Recles et al., "Most Probable Number Techniques" published in "Compendium of Methods for the Microbiological Examination of Foods", 3rd ed. 1992, at pages 105–199, and in Greenberg et al., "Standard Methods For the Examination of Water and Wastewater" 8th ed. 1992). In this method, a volume of sample is dispensed into several tubes representing this dilution range. The tubes are then incubated at the appropriate temperature so that the bacteria in each tube are allowed to grow after incubation at a specific temperature for a specific time, the number of positive tubes is counted. The most probable number can be determined from the formula described in Recles et al., supra.

Water testing is mostly done by membrane filtration, where a certain volume of water is passed through the membrane and the membrane is incubated in a medium for a certain period of time. After appropriate incubation, the colonies are counted.

Processes and products that allow for the identification and accurate enumeration of bacteria and other microbes would provide significant benefit to a variety of industries including, but not limited to, manufacturers of food products, cosmetics, and diagnostic assays.

BRIEF SUMMARY OF THE INVENTION

The present invention is directed generally to methods for detecting and quantifying microorganisms in a sample.

Prior to setting forth the invention, it may be helpful to an understanding thereof to set forth definitions of certain terms that will be used herein.

Definitions:

The term "incubation site" defines the area upon which the sample is incubated with the selective media. These sites may be in the shape of a petri-dish, at least one recessed well, within a vessel or a thin film culture plate device.

The term "target microbe" means one or more microbes whose presence or absence is to be determined. The term may refer to a single microbe (e.g., *Escherichia coli, Enterococcus faecalis, Staphylococcus aureus, Mycobacterium fortuitum*, and pneumonia), a genus of microbes, a number of related species of microbes, (e.g., coliforms), or even larger groups of microbes having a common characteristic (e.g., all gram negative bacteria).

The term "medium" refers to a solid, powder, or liquid mixture that contains all or substantially all of the nutrients necessary to support growth and reproduction of the target microbes. This invention includes media that is both sterilized (i.e., in which no growth results upon incubation of the media alone, or with a sterile diluent), as well as media which is not sterile.

The term "liquefied" refers to substantially in liquid form, although it is also meant to cover pulverized or homogenized samples of solid substances.

The term "detectable characteristic signal" includes any change in a sample which may be detected by either one of the human senses or by a machine.

The term "surface acting agent" refers to any molecule that acts to increase or decrease the surface tension of a liquid.

The term "nutrient indicator" means a molecule or substance containing a moiety that is a source of an essential nutrient for the target microbe, and a moiety which causes or produces an observable characteristic change in the selective medium or sample. A nutrient indicator may include, but is not limited to, nutrient sources attached to or conjugated to chromogens. Nutrient sources may provide essential vitamins, minerals (e.g., phosphate), trace elements, amino acids, or carbohydrate energy source (e.g., lactose). The nutritional requirement of a microorganism increases as the microorganism progresses from the phase in which nutrients are accumulated for reproduction (lag phase) into the phase during which reproduction actually occurs at a relatively rapid rate (log phase). Consequently, nutrient indicators are optimally metabolized during their growth periods which produces a detectable and characteristic change in the sample. Preferably, the nutrient indicator includes a nutrient moiety and a chromogen. Chromogens include any moieties that produce a color change observable in the visible range or fluorescence when properly excited by the proper energy source. Examples include, but are not limited to, orthonitrophenyl, phenolphthalein, and 4-methylumbelliferone moieties. Detectable characteristics may also include any change in a sample which may be detected by one of the human senses or read by a machine. These may include, but are not limited to, color change in the visible or non-visible wave length ranges, a change in the state of matter such as between solid, liquid, and gas, an emission of gas, or a change odor.

This invention provides a method for detecting and/or quantifying biological material in a sample. Such biological material include, but are not limited to, fungi or other living organisms, as well as aggregates of proteins, such as enzymes, or even co-factors, using reaction mixtures well known to those in the art. Biological material may further include coliforms, E. coli, and Enterobacteriaceae. The sample may be any biological sample or environmental sample such as wastewater, food, food source, a surface swab, or swabs from other surfaces, such as a throat, or other samples well known to those in the art. This sample may be a liquid sample, or may be dissolved in a liquid to form the liquefied sample. Thus, the term "liquefying" in the above paragraph refers to providing the sample in a liquid that once combined with a microbiological reagent can be rapidly aliquoted within the incubation vessel. The liquefied sample may remain as liquid or may be solidified in the incubation sites.

The present methods include the steps of liquefying the sample, if necessary and pouring the liquefied sample into an incubation vessel. This incubation vessel has a generally flat horizontal surface, wherein the surface has at least one incubation site. The incubation site may comprise any size or shape suitable for holding liquid such as in the form of a recessed well or a thin film culture plate device. The incubation site is adapted to hold an aliquot of liquid, and is sized and shaped, and formed of material that holds the aliquot within each incubation site. The aliquot is held by surface tension or by gelling the liquefied sample or by treating the surface of the incubation site chemically or physically to increase surface tension of the liquid. The incubation vessel containing the sample is then incubated for a period of time sufficient to determine the presence or absence of biological material in the sample. In the absence of any biological material, the incubation vessel does not provide a positive response.

In a related embodiment, the incubation vessel is covered in a waterproof substrate and/or formed of plastic. In a specific embodiment, the incubation vessel is formed of polyvinyl chloride. In yet another embodiment, the incubation vessel is formed of a polymer. In a specific embodiment, the incubation vessel is formed of a polymer selected from the group consisting polyester, polypropylene, and polystyrene. In yet another embodiment, the incubation vessel is formed of a hydrophobic material. In yet another embodiment, the incubation vessel of the present invention is circular in shape.

In a related embodiment, the horizontal surface defines at least 20, 40, 60, 90, 200, or more recessed incubation sites. In a related embodiment, the incubation areas of the present invention have a diameter of about 0.15 inches, and the incubation vessel has a diameter of about 3 to 5 inches. In a related embodiment, the incubation vessel holds a total of between about 1 to 100 mls of liquid.

In one embodiment, a lid is also provided to prevent contamination of the liquid within the incubation site, and the incubation vessel may also be provided in a sterile form so that no positive samples are detected unless at least one biological material particle is present in the sample. In a related embodiment, the incubation vessel is covered with a transparent film.

In yet another embodiment, the incubation vessel may be clear or colored. In a related embodiment, the incubation vessel may be a shade of white or yellow, to enhance the appearance of the any nutrient indicators present in the incubation media.

In one aspect, the present invention provides for an incubation vessel, wherein the incubation area is chamfered to aid in the removal of excess liquid.

In one aspect of the present invention, the liquid comprises a surface acting agent that either prevents the formation of bubbles in the liquid contained within the incubation area, and/or facilitates the removal of bubbles from the liquid once the liquid is placed within the incubation area. In a related embodiment, the sample or incubation site contains a surface acting agent selected from the group consisting of antifoaming agents, defoaming agents, detergents, surfactants, bile acids, and wetting agent. In yet another embodiment, the surface acting agent is selected from the group consisting of sodium dodecyl sulfate, Antifoam 204™ non-silicone organic defoamers in a polyol dispersion, available from Sigma Aldrich, USA), and Antifoam 289™ (non-silicone organic defoamers in a polyol dispersion, available from Sigma Aldrich, USA).

In yet another embodiment, the incubation vessel of the present invention incorporates a "landing pad", which is a generally central area of the incubation vessel lacking recessed wells, or incubation areas, which can receive the samples either prior to or after the sample is diluted in selective media, wherein the incubation media comprises a surface acting agent. Thus, a volume of sample liquid may be applied in the landing pad area (volume depends on the size and shape of the landing pad area), and the liquid dispensed into each of the incubation areas by applying the diluent and growth-supporting medium (e.g., the Colilert™ chemicals described herein) and that liquid may simultaneously dilute the sample and allow the dispersion of the sample throughout the incubation area.

In addition, the present invention provides for an incubation vessel that comprises a pour-off pocket adjacent to the surface of the incubation vessel, wherein the pour-off pocket contains excess liquid removed from the surface of the incubation vessel. In a related aspect, the pour-off pocket of the present invention contains an absorbent material, e.g., a gauze-like material. In a related embodiment, the present invention provides for an incubation vessel that has both a pour-off pocket and a landing pad.

In yet another embodiment, the present invention provides a kit for detecting a biological material in a sample, comprising; i) a self supporting, waterproof substrate to which is adhered a rehydratable selective medium that may be in any form, such as powder, containing nutrients which facilitate the growth of any biological material present in the sample; ii) a transparent cover sheet that has a layer of adhesive consisting essentially of a substrate system having an effective amount of one or more nutrient indicators provided in an amount sufficient to produce a detectable characteristic signal in the medium during growth of the biological material, and said nutrient indicator being operable to alter a detectable characteristic of the sample if metabolized in the presence of said biological material; iii) optionally a surface acting agent for use in reducing the introduction of air bubbles into the incubation vessel; iv) optionally at least one gelling agent; and v) instructions for using the kit for the detection of biological material is a sample.

In a related aspect, the surface acting agent of the kit is selected from the group consisting of anti-foaming agents, defoaming agents, detergents, surfactants, and bile acids. In yet another embodiment, the surface acting agent of the kit is selected from the group consisting of sodium dodecyl sulfate, Antifoam 204™ (non-silicone organic defoamers in a polvol dispersion, available from Sigma Aldrich, USA), and Antifoam 289™ (non-silicone organic defoamers in a polvol dispersion, available from Sigma Aldrich, USA).

In yet another embodiment, the gelling agent of the kit is selected from the group consisting of xanthan gum, locust bean gum, rhamsan gum, guar gum, and gellan.

In yet anther embodiment, the nutrient indicator of the present invention alters the color of the selective media in the presence of a viable biological material. In a related embodiment, the nutrient indicator of the present invention alters the color of the selective media in the visible wavelength range. In yet another related embodiment, the nutrient indicator is a β-D-glucuronidase substrate. In yet another embodiment, the β-D-glucuronidase substrate is selected from the group consisting of orthonitrophenyl-β-D-glucuronide, β-naphthalamide-D-glucuronide, α-naphthol-β-D-glucuronide, and 4-methylumbelliferyl-β-D-glucuronide. In yet another embodiment, the nutrient indicator is a β-galactosidase substrate. In a related aspect, the β-galactosidase substrate is selected from the group consisting of orthonitrophenyl-β-D-galactopyranoside and 4-methylumbelliferyl-β-D-galactopyranoside. In a further embodiment, the nutrient indicator of the present invention is a β-glucosidase substrate. In a related embodiment, the nutrient indicator is a L-pyronidonyl aminopeptidase substrate. In yet another embodiment, the nutrient indicator is a L-alanine aminopeptidase.

In a related aspect, the selective medium of the present invention further comprises an antibiotic that prevents non-target microbes from metabolizing said nutrient indicator.

In yet another embodiment the present invention provides for a method of detecting a biological material in a test sample comprising, using a kit comprising; i) a self supporting, waterproof substrate to which is adhered a rehydratable selective medium in any form, such as a powder, containing nutrients which facilitate the growth of target biological material present in the sample; ii) a transparent cover sheet that has a layer of adhesive consisting essentially of a substrate system having an effective amount of one or more nutrient indicators provided in an amount sufficient to produce a detectable characteristic signal in the medium during growth of the biological material, with the nutrient indicator being operable to alter a detectable characteristic of the sample if metabolized in the presence of said biological material; iii) optionally a surface acting agent for use in reducing the introduction of air bubbles into the incubation vessel; iv) optionally at least one gelling agent; and v) instructions for using the kit in the detection of biological material. Further, the method provides contacting the substrate of the kit with a test sample; and incubating the substrate and the test sample for a time sufficient to detect the presence of any target biological material.

In yet another aspect, the present invention provides for a culture medium comprising: i) an effective amount of vitamins, amino acids, elements and salt ingredients to allow viability and reproduction of the target microbe; ii) an effective amount of one or more nutrient indicators provided in an amount sufficient to produce a detectable characteristic signal in the medium during growth of the biological material, and said nutrient indicator being operable to alter a detectable characteristic of the sample if metabolized in the presence of said biological material; iii) optionally a surface acting agent for use in reducing the introduction of bubbles into the incubation vessel; and iv) optionally at least one gelling agent.

In yet another aspect, the present invention provides for a method for detecting a biological material in a sample comprising, contacting a rehydratable film with a sample and incubating for a period of time sufficient for the detection of the presence or absence of the biological material, wherein the method comprises contacting the film with the sample in the presence of a surface acting agent.

DETAILED DESCRIPTION OF THE INVENTION

Figure 1:
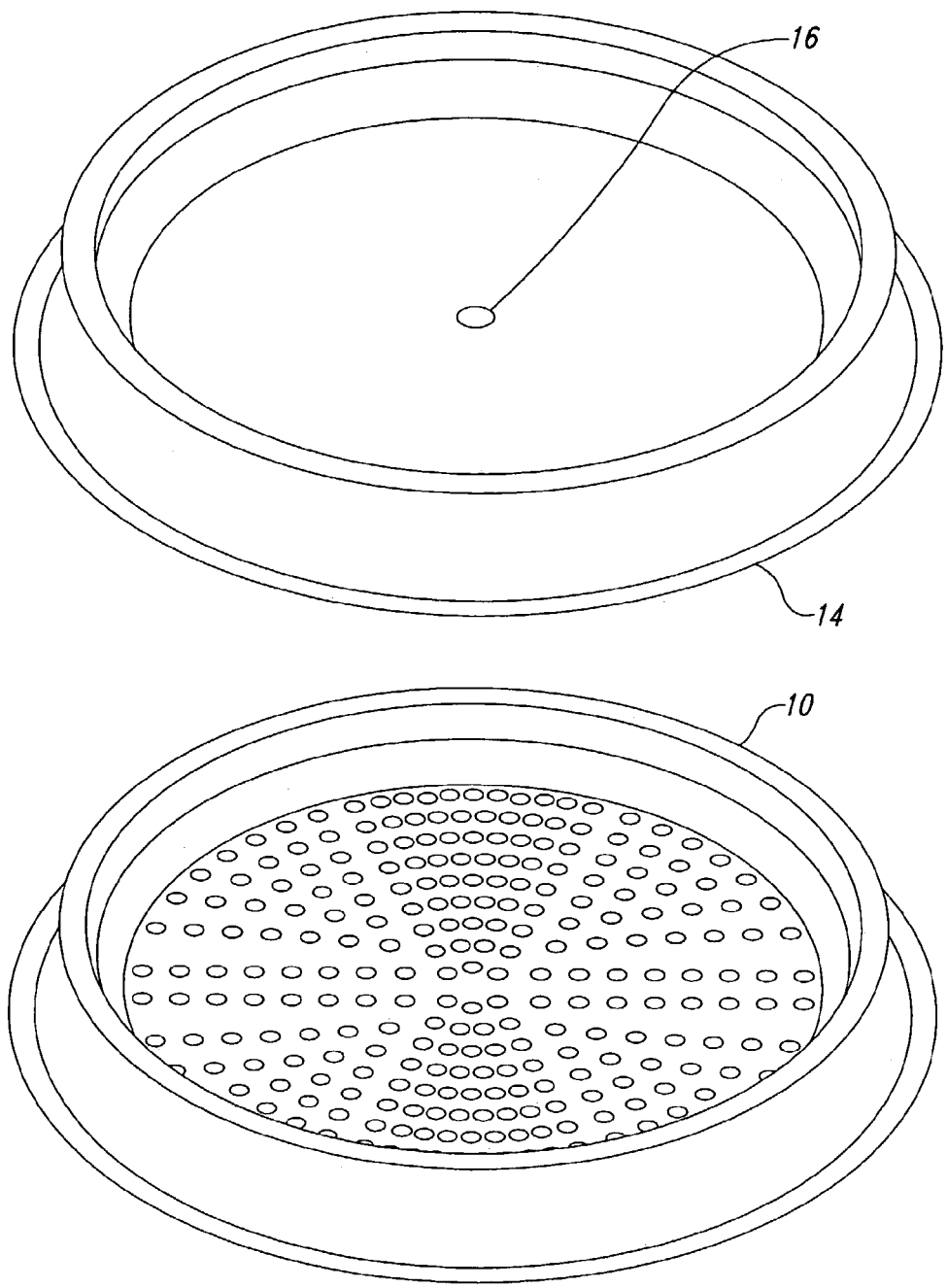
FIGS. 1 and 2 are diagrammatic representations of a formed plastic incubation vessel.

Herein, the present invention provides a novel and extremely useful method that allows unskilled personnel to rapidly determine the quantity of biological material within a sample. Liquefaction of the sample can be readily performed for use in the methods of the present invention without significant training in microbiology, and the materials for any specific tests can be provided by the manufacturer, allowing a person to readily perform the testing for microorganisms with accuracy. The incubation vessel is generally provided in sterile form so that no inappropriate detection of biological material can occur.

The present invention provides a simple method for the accurate quantification of the number of microorganism in a sample, or for quantification of any other type of discrete particulate biological material within a sample. Such biological materials include fungi or other living organisms, as well as aggregates of proteins, such as enzymes, or even co-factors, using reaction mixtures well known to those in the art. The invention generally makes use of a novel article that is designed to hold a liquid sample in which chemical and/or microbiological reactants are provided. For example, such chemical reactants may be a specific growth medium or selective medium for bacteria. The device used is generally in the form of an incubation vessel having at least one well or incubation area, each of which are designed to hold separate aliquots of liquid. Generally, the device is designed to hold between 5 and 100 ml of liquid in total, and the incubation sites are designed to form separate incubation chambers for each aliquot of sample. The incubation sites can be of same size or of different size and shape to increase counting range and/or simulate dilution effects. See Naqui et al., U.S. Ser. No. 08/201,110, filed Feb. 23, 1994, entitled "Apparatus and Method for Quantification of Biological Material in a Liquid Sample", incorporated by reference herein.

The incubation vessels of the present invention may either be in the shape of a petri-dish, a vessel containing at least one recessed well, or a thin film culture plate device, essentially similar to an Aerobic Count PERTIFILM culture plate device (commercially available from 3M, St. Paul Minn., catalog number 6400) or those described in U.S. Pat. No. 5,635,367. Indeed, the incubation vessel can be used to take the place of a petri-dish. Specifically, the method of this invention can be used to replace those existing tests that are generally run on petri dishes, to score the number of bacterial colonies. Since discrete aliquots of the sample are provided in the incubation vessel, one of ordinary skill in the art need only score the number of positive incubation areas in the incubation vessel to define the quantity of biological material within the original sample, as with-the MPN test described herein.

The generally flat horizontal surface is designed to allow the liquid to be distributed readily between the incubation areas and then excess liquid to be poured from the incubation vessel. In a preferred embodiment, a lip or pouring spout is provided for the incubation vessel. Those in the art will recognize that the depth and shape of the recessed wells, as well as the material used to make the wells, the incubation sites and the incubation vessel, are chosen such that surface tension can be used to hold the aliquots within each incubation site independent on the type of the liquid used in the liquefied sample.

The number of target microorganisms present in a sample may be quantified by mixing a liquid sample with a selective media. Selective medium may include suitable nutrients, salts and ions necessary for the growth requirements of the target microorganisms to be detected and quantified. The selective media may also contain inhibitors to prevent growth of other undesired microorganisms. Suitable nutrients, salts, and ions include casein peptone, yeast extract, beef extract, glucose, sodium pyrovate, disodium phosphate, monopotassium phosphate, ferric ammonium titrate and sodium carbonate. One of skill in the art would be able to readily ascertain additional ingredients that would be suitable nutrients, salts and ions for use in the growing selective microorganisms. Before use, the listed components are mixed or blended and then sterilized. Exposure to ethylene oxide or ultraviolet lights is sufficient to sterilize the components. Selective inhibitors are also included in the medium to prevent the growth of undesired microorganisms. Suitable inhibitors include a variety of well known antimicrobial or antibiotic compounds, readily determined by one of ordinary skill in the art.

Selective media can be provided in a dehydrated form and rehydrated using the liquefied sample, or other sterile solution. Alternatively, the selective media can be provided in a rehydrated form, either already present in the incubation vessel, or added to the incubation area prior to use.

When using a powdered form of the selective media, the media can be rehydrated with an appropriate amount of sterile liquid and then inoculated with a known volume of a test sample. For example, 20 ml of sterile water can be inoculated with between 10 and 1,000 microliter of sample. The inoculated reagent can then be added to-incubation vessel 10 and that liquid swirled within incubation vessel 10 to distribute the inoculated liquid reagent to each of the incubation sites 12. Incubation vessel 10 is then held at an angle of approximately 90 degrees to allow excess inoculated liquid reagent to be removed from the incubation vessel. A lid may then be placed on the incubation vessel and that vessel held in an incubator for the appropriate length of time, for example, but not limited 18–48 hours. The length of incubation time required will vary depending on the microorganism being tested for, and can be readily determined by one of ordinary skill in the art. After that length of time, the presence or absence of a positive result can be scored in each incubation area 12 of the incubation vessel. In addition, for incubation vessels having a "pour-off pocket", due to the larger volume of fluid contained in the pocket, a positive result in the pocket can serve as an early indication of high bacterial counts.

The selective medium of the present invention may also include substrates that allow the visual detection of different types of microorganisms. One such substrate is a glucopyranoside substrate that will react with a beta-glucosidase metabolite produced by bacteria. A variety of known beta-glucosidase-indicating compounds are commercially available, and readily identified by one of skill in the art.

The selective media of the present invention is generally mixed with gel-forming materials to give a solid medium. A solid medium provides a defined area for growth of bacterial colonies that may be present in a sample. Suitable gel forming materials include commercially available agar as well as methyl pectin, which are described in U.S. Pat. No. 5,210,022. Other gelling materials that can be used include, but are not limited to, gel-forming gums such as xanthan gum, locust bean gum, rhamsan gum, and guar gum, or mixtures thereof. One factor that may affect the results obtained when using culture systems to quantify the amount of biological material in a given sample is the introduction of voids and/or air bubbles into the incubation sites of the incubation device after addition of the liquefied sample. Such voids or air bubbles are time consuming to remove and can result in additional labor costs associated with running large number of tests in the laboratory. The presence of these air bubbles can be dramatically reduced by the presence of a surface acting agent in the liquid sample deposited on the device surface. Such an agent can be added to the sterile diluent used to prepare the test reagent, can be separately added to the test reagent after it is prepared, or can be added to the test sample directly while it is being prepared for testing.

For purposes of this invention, surface acting agents are defined as molecules which act to increase or decrease the surface tension of a liquid, in some way break apart air bubbles in a liquid sample, or facilitate entry of liquid into the recessed wells of the device of this invention. For example, a surfactant such as sodium dodecyl sulfate (SDS) acts to reduce or break the surface tension of a liquid. If SDS is present in a liquid at a concentration of approximately 0.01% it will reduce the surface tension of the liquid, thus, causing it to uniformly flow into the incubation sites of the device described in this invention. The net effect of this is that fewer air bubbles or voids exist in the recessed wells of the device than are present when SDS is not present in the liquid. The same effect can be produced with other surface acting agents, which include, but are not limited to defoamers, surfactants, bile acids, or any other molecule that decreases the surface tension of the liquid.

In one aspect of the present invention, the surface acting agent is added to the diluent used to prepare the test reagent. Examples of such surface acting agents, include, but are not limited to, antifoam 204 or antifoam 289 can be added to sterile deionized water at a final concentration of 0.01%. This sterile diluent can be used to prepare the test reagent by adding the sterile test reagent powder directly to the sterile diluent. This solution is then mixed. After mixing, the test reagent may be applied to the incubation device/vessel described in this invention. The presence of the surface acting agent will facilitate efficient flow of fluid into the incubation sites of the incubation vessel resulting in less labor time being spent operating the test. It should be obvious to those skilled in the art that certain surface-acting agents will perform better than others at reducing incomplete fluid flow into the device of this invention. Furthermore, it is anticipated that other molecules may be discovered that can be added to the liquid test reagent to enhance the performance of the test by reducing the amount of time spent introducing the liquid into the incubation sites and/or removing excess liquid from the device.

Such an agent can be added to the sterile diluent used to prepare the test reagent, can be separately added to the test reagent after it is prepared, or can be added to the test sample directly while it is being prepared for testing. Surface acting agents of the present invention can be used into other testing methods to reduce the amount of air bubbles or voids that can interfere with the reading of the test results (See U.S. Pat. No. 5,625,367). One such application is with dry rehydratable film methods. Many of the dry rehydratable film methods rely on the production of one or more gas bubbles to detect target microorganisms. For example, the dry rehydratable film method for *E. coli* detects the presence of total coliforms and *E. coli* by the presence of gas bubbles around typical coliform colonies. When setting up of the test, accidental introduction of air bubbles can occur, which make reading the tests difficult and can result in erroneous results. Introduction of a surface acting agent like those just described herein can significantly enhance the performance of the dry rehydratable film method tests by only allowing gas bubbles to appear which are the result of microbial metabolism and not accidental introduction by the laboratory technician.

While it is known to provide plastic containers that can hold liquid within a plurality of recesses, applicant believes that this device provides a new automatic aliquoting method. This is an improvement over the existing products used to detect and quantify microorganisms because the liquid migrates to the individual sites without individual dispensing.

Figure 2:
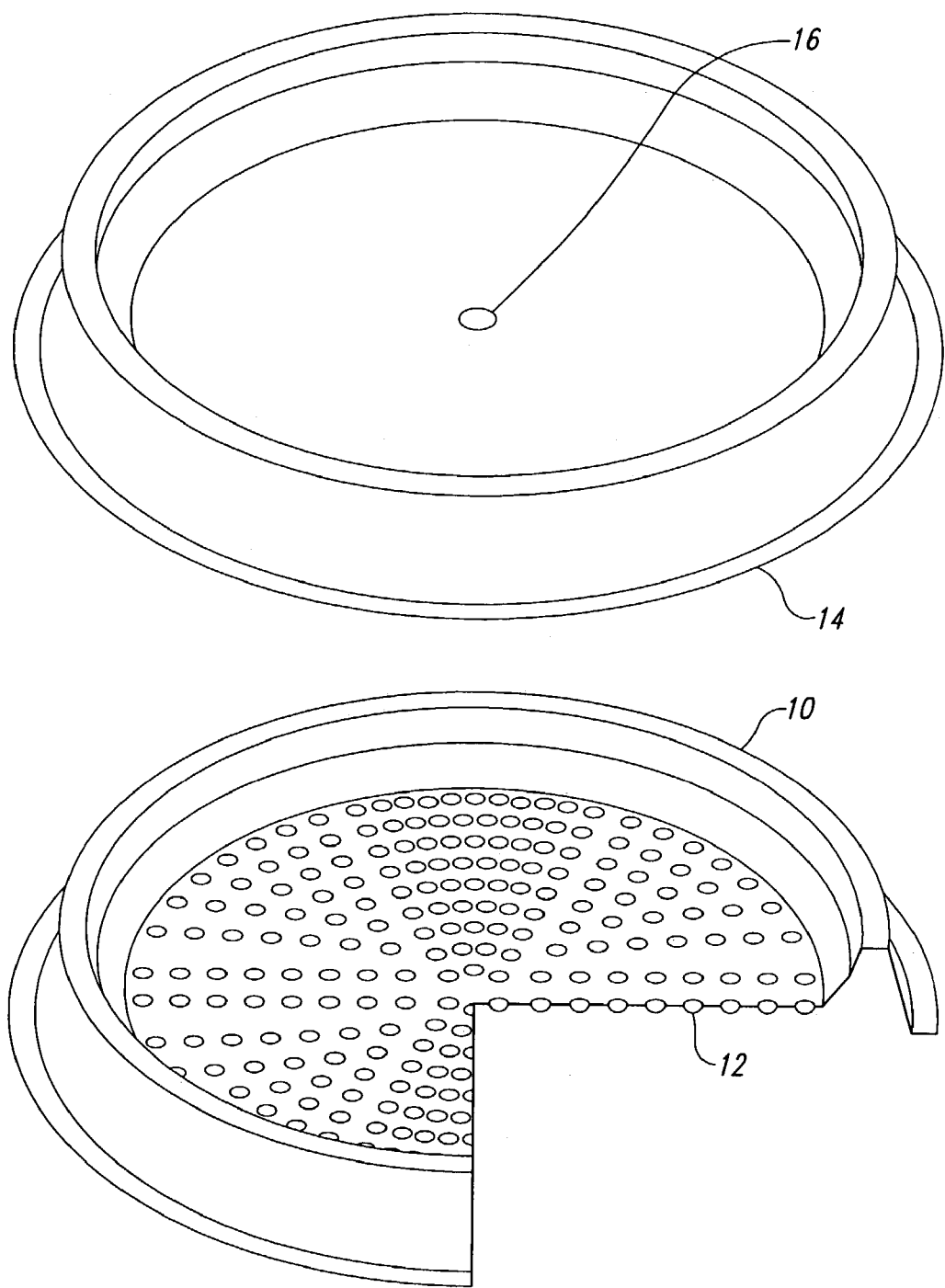
Figure 3:
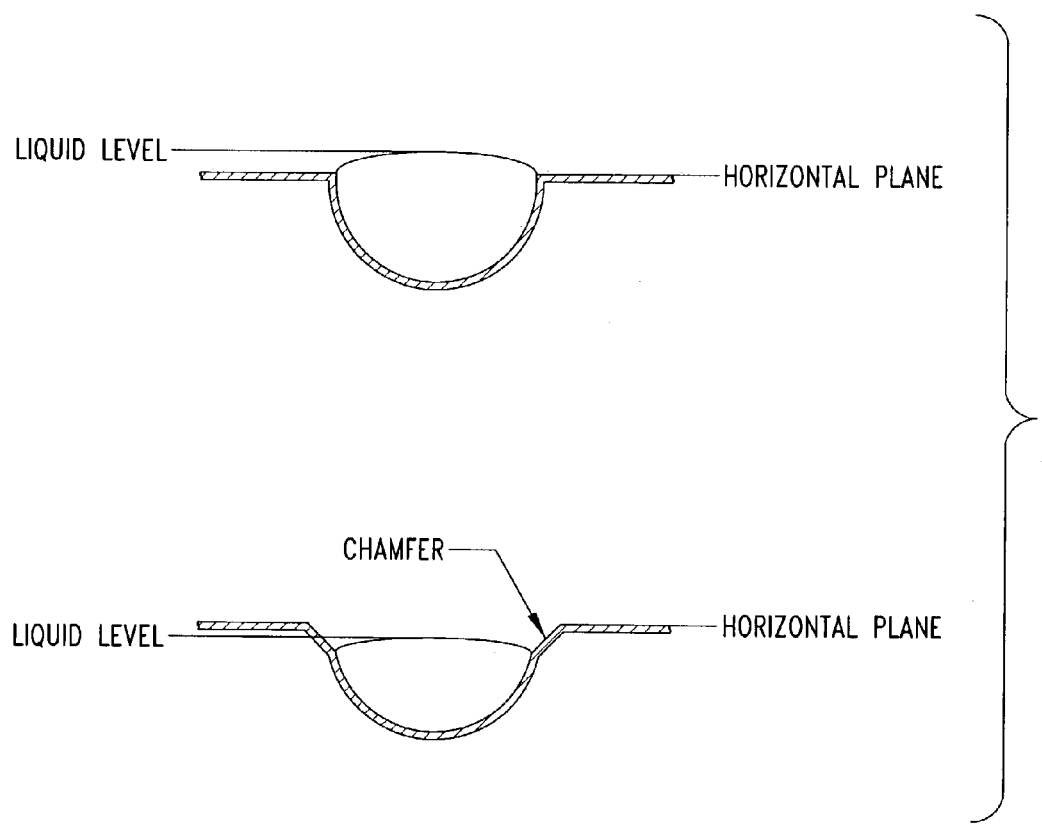
FIG. 3 shows a cross section of a well, with or without a chamber.

The present device can replace the use of a petri dish and can be used particularly in food analysis and in testing of clinical samples. The separation of the incubation sites of the present device prevents crosstalk or contamination between each aliquot. This feature allows many of the tests to be performed by observing fluorescence (which is not readily performed in an agar-containing petri dish). The device is particularly useful when there is a large quantity of microorganisms present in a sample, such as more than one organism per one ml or per ten ml, and when it is helpful to reduce or eliminate air bubbles in a particular testing sample. Other features and advantages of the invention will be apparent from the following description of the preferred embodiments thereof, and from the claims. Referring to FIGS. 1 and 2 there is shown an incubation vessel 10 having a plurality of incubation sites (wells) 12 each having a diameter of about 0.16 inches. The incubation vessel 10 has a diameter of about 5 inches. The incubation vessel is made of formed plastic. Incubation sites 12 are spaced apart sufficiently to prevent cross talk between the incubation sites. These incubation sites may have a chamfer (FIG. 3) if desired to prevent liquid remaining at the upper edge of the incubation sites. Those in the art will recognize that incubation vessel 10 can be readily formed by standard procedure and manufactured in the general shape of a petri dish, with or without a lip or pouring spout, and with or without a lid 14. This lid is provided with a dimple 16 to prevent contact of the lid with incubation vessel 10.

Figure 4:
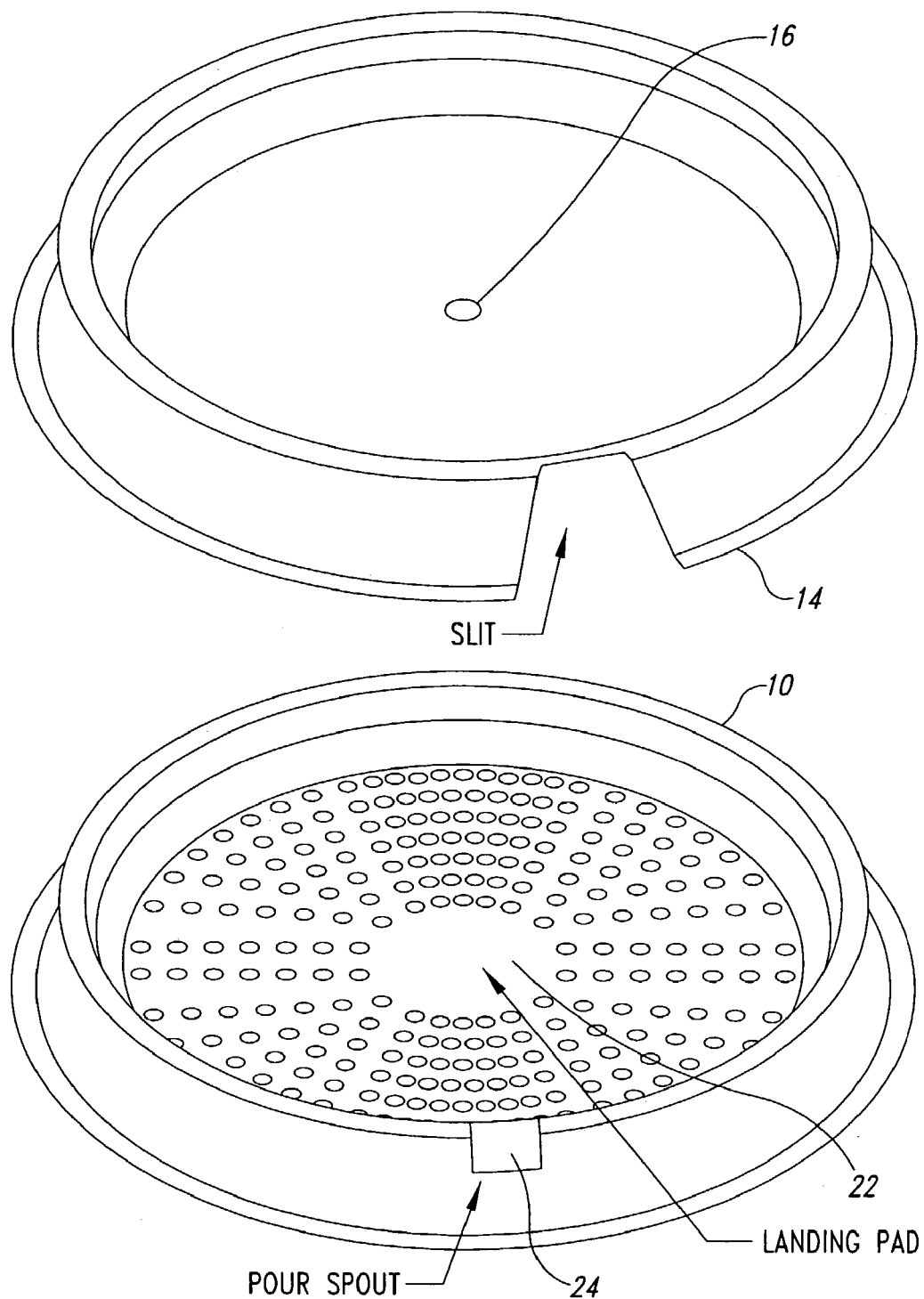
FIG. 4 is a diagrammatic representation of a formed plastic incubation vessel having a pour spout and corresponding slit as well as a "landing pad".

Referring to FIG. 4, there is shown in incubation vessel 10 having a plurality of incubation sites much as described above. The incubation vessel also includes a "landing pad" 22 of size about one and one-half inch diameter which is simply an area able to hold a defined volume of liquid. Within the incubation vessel is also is provided a pour spout 24 which allows excess liquid to be removed from the incubation vessel. Also provided is a corresponding lid 14 having a slit which can be matched with the pour spout to allow liquid to be removed from the incubation vessel. When the slit is not aligned with the pour spout, reducing airflow over the liquid in the incubation sites decreases evaporation of liquid within the incubation vessel. A dimple 16 may also be provided in the lid to prevent the lid surface contacting the incubation sites and thus preventing cross contamination between the incubation sites.

Figures 5A, 5B:
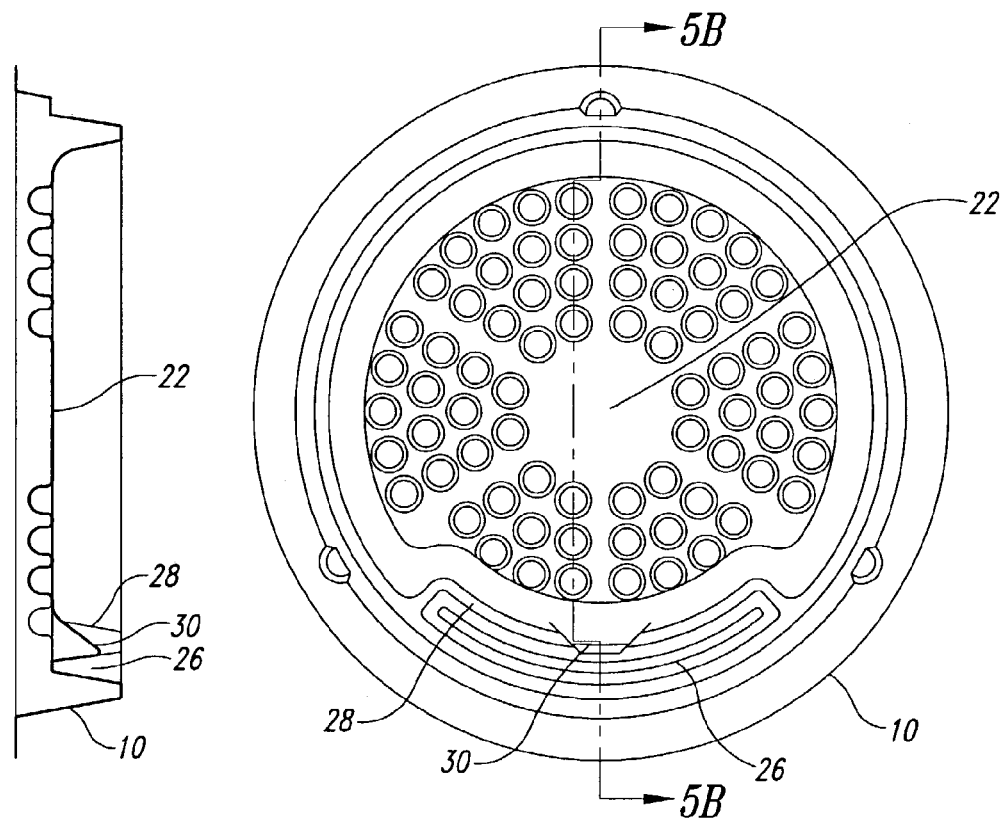
FIGS. 5A and B are a diagrammatic representation of a formed plastic incubation vessel having a "landing pad" and a "pour-off pocket".

Referring to FIG. 5, there is shown an incubation vessel 10 having a plurality of incubation sites much as described above, which also includes a "landing pad" 22 of size about one inch diameter. Within the incubation vessel is also provided a "pour-off pocket" 26 adjacent to the surface of the incubation vessel which allows excess liquid to be removed from the incubation vessel. As shown in the cross-sectional view, the "pour-off pocket" is formed by an elevated barrier 28 between the pocket and the incubation vessel surface. The barrier has a lower barrier section 30, which serves as a channel through which the excess fluid from the incubation vessel surface may be poured into the pocket. Typically, the pocket will contain an absorbent material that will retain the fluid within the pocket, preventing back spill onto the incubation vessel surface.

The following examples are provided to further illustrate the practice of the various embodiments of the present invention. The examples are provided for illustrative purposes only and should not be construed to limit the scope of the invention, which is set out in the appended claims or the specification.

EXAMPLE 1

Use of Incubation Vessel for Bulk Testing

For total plate count an incubation vessel as described above is used for the detection and quantification of the total bacterial concentration of food. It is based on a Multiple Enzyme Technology (Townsend and Chen, Method and Composition for Detecting Bacterial Contamination in Food Products, U.S. Ser. No. 08/484,593 hereby incorporated by reference herein) that correlates enzyme activity to the presence of viable bacteria in food. It utilizes multiple enzyme substrates that produce a blue fluorescent color when metabolized by bacteria. When the liquid reagent is inoculated with a prepared food sample and-dispensed into an incubation vessel as described herein the total viable bacterial concentration of that food product can be determined after 24 hours of incubation. The actual medium used herein is not critical to the invention, but is provided only for illustrative purposes.

Storage and Disposal

Store bulk powder and unused Simplates at room temperature (4 to 25° C.) away from the light. After use, the Simplate device will contain viable bacteria that must be handled and discarded appropriately. Once the powder is rehydrated it is stable for up to 24 hours when stored at 4 to 25° C.

Test Procedure

1. Pour an appropriate amount of bulk powder to a container of sterile deionized water. One vial contains enough powder for 10 tests. Each test has a final volume of 10 ml. For example: add 1 vial of powder to 100 ml of sterile water to make enough media for 10 tests.

2. Place test sample on the center "landing pad" 22 of the incubation vessel 10 shown in FIG. 4. At the completion of this procedure half of the test sample will be poured off and discarded, therefore, the size of the inoculum must take this into account. For example, if you wish to measure the bacterial concentration of 0.1 ml of test sample then you must place 0.2 ml of test sample on the "landing pad". Place no more than 2 ml on the center of the "landing pad".

3. Remove the lid from the incubation vessel and dispense 10 ml of TPC media in the incubation vessel making sure to direct the liquid over the test sample on the center "landing pad". If the test sample is greater than 0.1 ml add enough TPC to achieve a final volume of 10 ml in the incubation vessel. Note, if the liquid is not dispensed on the "landing pad" it may splatter.

4. Place the lid back on the incubation vessel. Note, to ensure that the liquid remains in the Simplate make sure that the slit on the lid is not lined up with the pour spout.

5. Distribute the liquid into the incubation sites by swirling the incubation vessel as you would a standard pour plate.

6. Line up the slit on the lid with the pour spout and carefully pour off the excess liquid that did not end up in the incubation sites. Holding the incubation vessel at an angle of approximately 90° from the work bench ensures proper pour off of excess liquid. Make sure that all liquid "cross bridges" between incubation sites are removed by gently tapping the incubation vessel. Dispose of excess liquid appropriately.

7. Slide the lid away from the pour spout to avoid drying the liquid in the incubation sites during incubation and to avoid contamination from outside through the opening.

8. Place the incubation vesselin an incubator for 24 hours. Incubation vessel can be inverted if desired. Incubation temperatures greater than 37° C. are not recommended.

9. Count the number of fluorescent incubation sites after 24 hours by placing a 6 watt 36 nm UV light within five inches of the incubation vessel. Do not read incubation vessel before 24 hours. Results are stable to 48 hours.

10. Compare the number of fluorescent incubation sites to an MPN chart to determine the most probable number of bacteria present in the incubation vessel.

Test Procedure Using incubation Vessel Having "Pour-Off Pocket"

1. Pour an appropriate amount of bulk powder to a container of sterile deionized water. One vial contains enough powder for 10 tests. Each test has a final volume of 10 ml. For example: add 1 vial of powder to 100 ml of sterile water to make enough media for 10 tests.

2. Place test sample on the center "landing pad" 22 of the incubation vessel 10 shown in FIG. 5. At the completion of this procedure half of the test sample will be poured off into the pocket, therefore, the size of the inoculum must take this into account. For example, if you wish to measure the bacterial concentration of 0.1 ml of test sample then you must place 0.2 ml of test sample on the "landing pad". Place no more than 2 ml on the center "landing pad".

3. Remove the lid from the incubation vessel and dispense 10 ml of media in the incubation vessel making sure to direct the liquid over the test sample on the center "landing pad". If the test sample is greater than 0.1 ml add enough media to achieve a final volume of 10 ml in the incubation vessel. Note, if the liquid is not dispensed on the "landing pad" it may splatter.

4. Distribute the liquid into the incubation sites by swirling the incubation vessel as you would a standard pour plate, taking care that the fluid does not enter the "pour-off pocket".

5. Carefully pour off the excess liquid that did not end up in the incubation sites through the "pour-off pocket" barrier channel. Holding the incubation vessel at an angle of approximately 90° from the work bench ensures proper pour off of excess liquid. Make sure that all liquid "cross bridges" between incubation sites are removed by gently tapping the incubation vessel.

6. Place the incubation vessel in an incubator for 24 hours. Incubation vessels can be inverted if desired if the "pour-off" pocket contains an absorbent material.

7. Count the number of fluorescent incubation sites after 24 hours by placing a 6 watt 36 nm UV light within five inches of the incubation vessel. Do not read incubation vessel before 24 hours. Results are stable to 48 hours.

8. Compare the number of fluorescent incubation sites to an MPN chart to determine the most probable number of bacterial present in the incubation vessel.

EXAMPLE 2

Use of Incubation Vessel for Unit Dose Testing

The incubation vessel and media described in Example 1 are used for this test.

Test Procedure

1. Add 10 ml of sterile water to the tube of pre-dispensed powder. If greater than 0.1 ml of food sample is to be inoculated into the test, reduce the volume of sterile water appropriately to achieve a final volume of 10 ml in the tube.

2. Inoculate the liquid reagent with the food sample being tested.

3. Shake tube several times to completely mix powder and inoculated food sample. Avoid excessive mixing which tends to foam up liquid reagent. Too much foam can complicate the distribution of the liquid into the incubation vessel. The rest of the procedure is as in Example 1.

Other embodiments are within the following claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for detecting a biological material in a liquid or liquefied sample comprising pouring the liquid or liquefied sample into an incubation vessel having a generally flat horizontal surface, said surface having at least one incubation site, said incubation site holding an aliquot of liquid and being sized and shaped, and formed of material which holds said aliquot within each incubation site, wherein said aliquot is held by surface tension or by gelling said liquid or by treating the surface chemically or physically to increase tension of said liquid, incubating said incubation vessel for a period of time sufficient to determine the presence or absence of said biological material in said biological sample, wherein said incubation vessel does not provide any positive response for said biological material in the absence of said biological material being present in said sample applied to said incubation vessel.

2. The method of claim 1, wherein said surface defines at least 20 incubation sites.

3. The method of claim 1, wherein said surface defines at least 40 incubation sites.

4. The method of claim 1, wherein said surface defines at least 60 incubation sites.

5. The method of claim 1, wherein said surface defines at least 90 incubation sites.

6. The method of claim 1, wherein said surface defines at least 200 incubation sites.

7. The method of claim 1, wherein said incubation vessel is covered in a waterproof substrate.

8. The method of claim 1, wherein said incubation vessel is formed of plastic.

9. The method of claim 8, wherein said plastic is polyvinyl chloride.

10. The method of claim 1, wherein said incubation vessel is formed by a polymer selected from the group consisting of, polyester, polypropylene, and polystyrene.

11. The method of claim 1, wherein said incubation vessel is formed of a hydrophobic material.

12. The method of claim 1, wherein said incubation vessel is generally circular in shape.

13. The method of claim 1, wherein said incubation vessel is provided with a lid to prevent contamination of liquid in said incubation vessel.

14. The method of claim 1, wherein said incubation vessel is covered with a transparent film.

15. The method of claim 1, wherein said incubation vessel is clear.

16. The method of claim 1, wherein said incubation vessel is colored.

17. The method of claim 16, wherein said color is yellow.

18. The method of claim 1, wherein said incubation site is about 0.15 inch in diameter.

19. The method of claim 1, wherein said incubation site is chamfered to aid in the removal of excess liquid.

20. The method of claim 1, wherein said incubation vessel is about three inches in diameter.

21. The method of claim 1, wherein said incubation vessel is about five inches in diameter.

22. The method of claim 1, wherein each said incubation vessel holds a total of between 1 and 100 ml.

23. The method of claim 1, wherein the incubation vessel is sterile.

24. The method of claim 1, wherein said liquid comprises a surface acting agent.

25. The method of claim 24, wherein said surface acting agent is selected from the group consisting of antifoaming agents, defoaming agents, detergents, surfactants, and bile acids.

26. The method of claim of claim 24, wherein said surface acting agent is selected from the group consisting of sodium dodecyl sulfate and an antifoam agent.

27. The method of claim 1, wherein said incubation vessel further comprises a pour-off pocket adjacent to said surface of said incubation vessel, wherein said pocket contains excess liquid removed from said surface of said incubation vessel.

28. The method of claim 1, wherein said incubation vessel comprises a landing pad which holds a sample prior to aliquoting of said sample to said incubation site.

29. The method of claim 28, said incubation vessel further comprising a pour-off pocket adjacent to said surface of said incubation site, wherein said pocket contains excess liquid removed from said surface of said incubation vessel.

30. The method of claim 1, wherein said biological material is selected from the group consisting of coliforms, *E. coli*, and Enterobacteriaceae.

* * * * *